(12) United States Patent
Zubova et al.

(10) Patent No.: US 6,419,689 B1
(45) Date of Patent: Jul. 16, 2002

(54) METHOD FOR PROTECTING A PERSON AGAINST THE ACTION OF ARTIFICIAL ELECTROMAGNETIC RADIATION AND DEVICE FOR REALIZING THE SAME

(76) Inventors: Nataliya Borisovna Zubova; Irena Igorevna Stjuart; Peter Igorevich Stjuart, all of 2-324 Bolshaya Tulskaya Street, Moscow 113191 (RU)

( * ) Notice: Subject to any disclaimer, the term of this patent is extended or adjusted under 35 U.S.C. 154(b) by 0 days.

(21) Appl. No.: 09/445,842
(22) PCT Filed: Apr. 15, 1998
(86) PCT No.: PCT/RU98/00109
§ 371 (c)(1),
(2), (4) Date: Jan. 6, 2000
(87) PCT Pub. No.: WO99/53501
PCT Pub. Date: Oct. 21, 1999
(51) Int. Cl.$^7$ .............................. A61N 1/16; G12B 17/00
(52) U.S. Cl. ................................................ 607/1; 607/2
(58) Field of Search .............................. 607/1, 2, 62, 76

(56) References Cited

U.S. PATENT DOCUMENTS 5,817,138 A * 10/1998 Suzuki ........................ 607/67

6,212,432 B1 * 4/2001 Matsuura ..................... 607/76

FOREIGN PATENT DOCUMENTS

| DE | 32 20 565 A1 | 12/1983 | ............. A61N/1/16 |
| DE | 33 22 396 A1 | 1/1985 | ............. A61N/1/16 |
| RU | 2033819 C1 | 4/1995 | ............. A61N/1/16 |
| RU | 2074748 C1 | 3/1997 | ............. A61N/1/16 |
| WO | 96/03178 | 2/1996 | ............. A61N/1/16 |

* cited by examiner

*Primary Examiner*—Carl Layno
(74) *Attorney, Agent, or Firm*—Ratner & Prestia

(57) ABSTRACT

Protection of man from artificial electromagnetic radiation is achieved through affecting the thymus with a low-frequency electromagnetic field at a frequency corresponding to that of the Shuman wave.

The method implementation device contains a generator (1) connected to a transmitting antenna (2), a comparator (3) and a logical bloc (4). The generator (1) serves as source of an electromagnetic field with an oscillation frequency corresponding to that of the Shuman wave oscillations. The intensity of the electromagnetic field is adjusted with the help of the logical bloc (4), which processes the signal from the comparator (3) comparing the current voltage between the acupunctural thymus projection points of the patient with the optimal value.

2 Claims, 1 Drawing Sheet

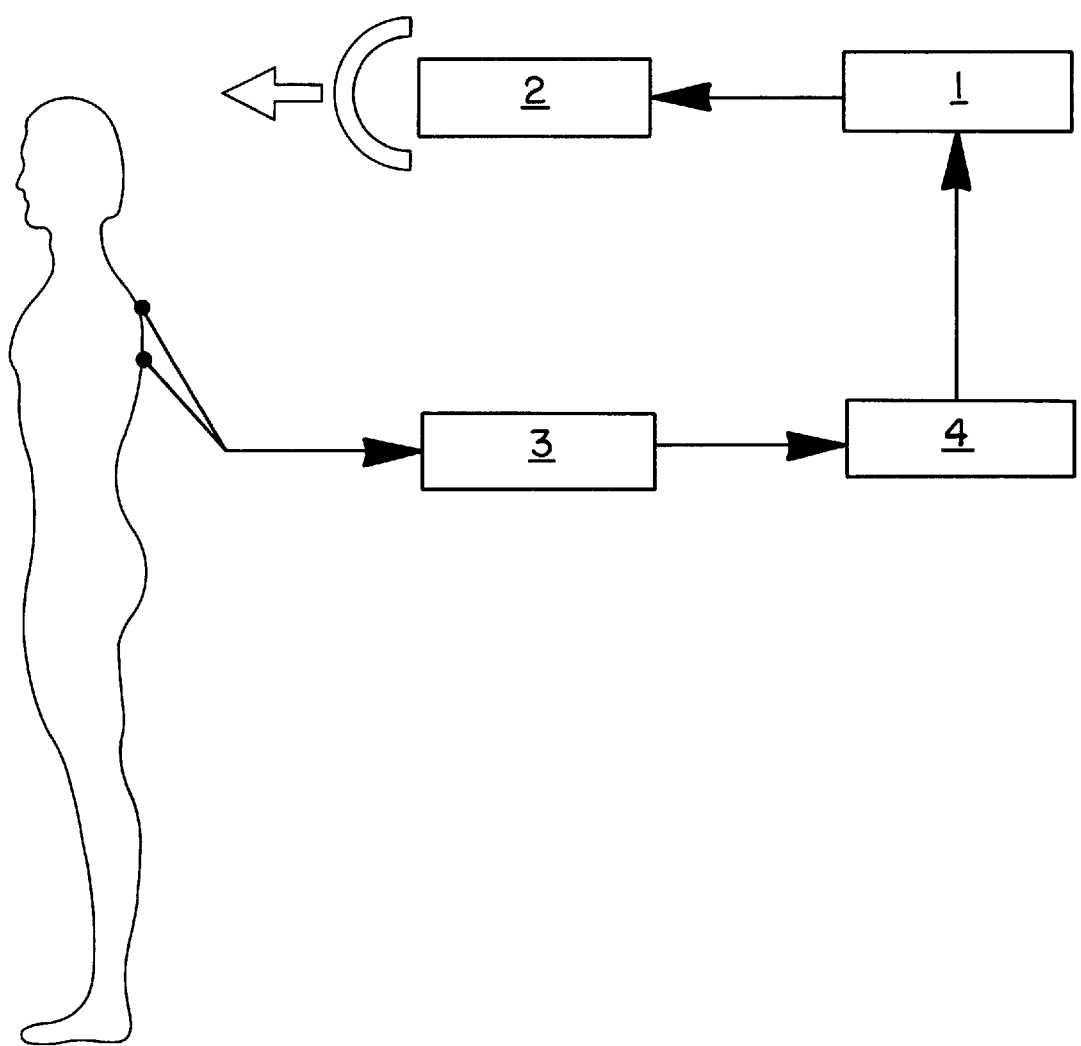

METHOD FOR PROTECTING A PERSON AGAINST THE ACTION OF ARTIFICIAL ELECTROMAGNETIC RADIATION AND DEVICE FOR REALIZING THE SAME

TECHNICAL FIELD

The invention applies to the field of medicine and medical equipment and can be used for protecting living organisms from the effects of artificial electromagnetic radiation, which cause serious physiological and functional problems, thus being dangerous for human health and life.

BACKGROUND OF THE INVENTION

The known methods of protecting man from artificial electromagnetic radiation and related implementation devices are based on creating sources of electromagnetic fields to offset the oscillations of artificial electromagnetic fields.

There is, for example, a device for balancing the surrounding electromagnetic field, where several electromagnetic field sources are used to produce balancing oscillations and offset the dangerous radiation emanating from cathode-ray tube (CRT) screens and motor vehicles. The device can be installed on vehicles and should contain at least three radiation sources to balance the electromagnetic field. (USSR patent No. 1718710, A61 N 1/16, publ. in 1992).

The above device and the related method do not ensure protection from other radiation of unnatural origin (high-voltage transmission lines, television and radio stations, radar equipment, mobile phones, etc.).

There are also protection devices using a high-frequency arc converter or a gas-discharge generator as a source of electromagnetic field oscillations.

These devices provide a local zone of compensating different types of artificial radiation.
(RF patent No. 2033200, A61N 1/16, publ. in 1995; RF patent No. 2071366, A61N 1/16, publ. in 1997).

These devices and the method they put into practice do not ensure effective protection from artificial electromagnetic fields, since they form a local compensation zone, inside which dangerous electromagnetic radiation emanated by high-voltage equipment is suppressed.

There are devices to protect man from artificial electromagnetic radiation, which contain a low-frequency electromagnetic-wave generator connected to an oscillator. (French application No. 2486406, A61N 1/16, publ. in 1983).

In these devices, the generator frequency lies within the range of 1–1000 Hz. The generator operation in these devices, however, is supposed to cover quite a wide range, and there is no bloc to generate a one-frequency wave for a prolonged period of time, with the frequency equal to that of the Shuman wave.

A method and device for protection of man from electromagnetic radiation (useful model No. 1805, A61 N 1/16, publ. in 1996) has been selected as the closest analog. The method provides for treating a man with a pulsating electromagnetic field with a fixed oscillation frequency within the 3–12 Hz range.

The device contains a square-wave generator connected to an antenna, with the generator fixed frequency being in the range of 3–12 Hz.

Nevertheless, the said method and device do not provide an effective protection from electromagnetic oscillations,. since a fixed source frequency for creating an electromagnetic field is not formed.

The objective of the invention consists in achieving a higher effectiveness of protecting man from the influence of artificial electromagnetic oscillations.

BRIEF SUMMARY OF THE INVENTION

A biological object represents an open system receiving EM oscillations emanated by different sources and forming its own EM oscillations.

The human organism has a certain range of vibrations with the amplitude and frequency characteristics liable to produce different pathologies.

Biological objects can feel EM oscillations within a range covering the whole of nonionizing wave spectrum. The organisms contains highly organized systems of perception, sorting, distribution of and reacting to specific EM wave ranges and trains, as well as to its proper vibrations coherent with the geomagnetic field of the Earth, which are emanated at a frequency corresponding to that of the Shuman wave.

A biological object can be regarded as a complicated structure of interconnected systems and subsystems that are in constant harmonic and non-linear interaction with one another.

A disease can be regarded as a break in the harmonic synchronization or balance in a biological object produced by various sources of clashing EM oscillations which endanger the normal functioning of the organism.

The easiest method consists in using identical reversed EM oscillations to produce a zero algebraic sum of the disharmonic and inverted EM oscillations. Organs and systems can be stimulated only in case we know the requirements to the EM oscillation characteristics capable of restoring the normal functioning of the damaged organs or systems.

The human thymus is very sensible to physical external influence to which it reacts by serious physiological and functional disbalance.

You will see below a list of biological effects caused by artificial electromagnetic oscillations irrespective of frequency:
- effect on the growing cells, for example, a higher cancer cell fission rate;
- a growing number of certain carcinogenic diseases;
- embryonic growth problems;
- psychic troubles caused by neuro-chemical changes;
- a growing number of other degenerate diseases (e.g. the Parkinson disease);
- trainability problems.

The destructive effects of artificial EM fields can be considerably reduced by treating the human thymus with a special pulsating electromagnetic field with oscillations at a fixed frequency corresponding to that of the Shuman wave, which regulates the functioning of all the other endocrine glands and brings about self-regulation of all the human organs.

The method of protecting man from the effect of artificial electromagnetic radiation is realized in a device generating an electromagnetic field with a fixed low frequency equal to the oscillation frequency of the Shuman wave.

The resultant medical effect is due not to the neutralization of harmful electromagnetic radiation (interference) effecting the thymus, but to constant restoration and stabilization of its functions (with dominating electromagnetic radiation at the thymus proper resonance frequency).

The device contains a generator of electromagnetic waves, connected to an oscillator—a transmitting antenna, a comparator comparing the current voltage between the acupunctural thymus projection points with the optimal value, whose outlet is connected to a logical bloc adjusting the electromagnetic radiation intensity of the device.

BRIEF DESCRIPTION OF THE DRAWINGS

The drawing represents a structural electrical circuit for protecting man from artificial electromagnetic radiation.

The device is composed of a low-frequency signal generator 1, a transmitting antenna 2, a comparator 3 and a logical bloc 4.

DETAILED DESCRIPTION OF THE INVENTION

EXAMPLE 1

Generator 1 emits a low-frequency signal at a fixed frequency equal to that of the Shuman wave 7.8 Hz, which corresponds to the thymus vibration frequency, and transmits the signal to the antenna 2, which emits an electromagnetic field stimulating the thymus and restoring its functions in case there was a pathology. To achieve the maximum medical effect, the intensity of the electromagnetic field being formed is adjusted with the help of logical bloc 4 processing the signal from comparator 3, which compares the current voltage ($U_{th}$) between the patient's acupunctural thymus projection points with the optimal value ($U_{th.opt}$).

EXAMPLE 2

Individual Option.

To protect himself from the effects of artificial electromagnetic oscillations, the patient places the device at a distance of 0.5–1.5 m from the body surface, when he stays in an electromagnetic radiation zone. He turns the switch, the indicator is on, and the device begins forming an electromagnetic field, which effects the thymus at a frequency equal to that of its proper vibrations. On quitting the electromagnetic radiation zone, the patient switches the device off. The operation time is unlimited.

EXAMPLE 3

Stationary Option.

The device is placed in a closed room. The operation range is 60 m. When the device is switched on, the generator starts to form a signal at a fixed frequency equal to the frequency of the Shuman wave. The antenna emits electromagnetic oscillations at the frequency of the patients' thymus proper vibrations.

Thus, the device protects the man from the negative effects of domestic and industrial electromagnetic radiation which pollutes the environment, such as daylight illumination lamps, colour TV, microwave ovens, proximity of high-voltage transmission lines, television and radio stations, radar equipment, frequent air flights, mobile phones, ground communications, metro lines, etc.

Industrial Applicability

The device is fed from a battery or the mains and can be equipped with an alarm system to show the existence of an electromagnetic field with a certain frequency. The device effectively operates within a range of not more than 1–60 m from the man's location.

What is claimed is:

1. A method of protecting man from artificial radiation, which consists in treating him with a low-frequency electromagnetic field, distinct in the low-frequency electromagnetic field oscillation frequency being the same as the frequency of the Shuman wave vibrations.

2. A device for protecting man from artificial radiation, containing a low-frequency signal generator, having an outlet, with the outlet connected to a transmitting antenna, distinct in the generator being capable of emitting electromagnetic oscillations at the Shuman wave vibration frequency, and the device being equipped with a logical bloc to adjust the electromagnetic intensity of the device, while a comparator is connected to the input of the logical bloc.

* * * * *